US00PP16441P2

(12) United States Plant Patent
Arts

(10) Patent No.: US PP16,441 P2
(45) Date of Patent: Apr. 11, 2006

(54) ***HYDRANGEA* PLANT NAMED '200749077'**

(50) Latin Name: *Hydrangea hybrida*
Varietal Denomination: 200749077

(75) Inventor: Niels Arts, Aalsmeer (NL)

(73) Assignee: HBA, De Kwakel (NL)

( * ) Notice: Subject to any disclaimer, the term of this patent is extended or adjusted under 35 U.S.C. 154(b) by 72 days.

(21) Appl. No.: 11/077,410

(22) Filed: Mar. 10, 2005

(51) Int. Cl.
*A01H 5/00* (2006.01)

(52) U.S. Cl. ..... Plt./250
(58) Field of Classification Search ..... Plt./250
See application file for complete search history.

*Primary Examiner*—Anne Marie Grunberg
(74) *Attorney, Agent, or Firm*—C. A. Whealy

(57) ABSTRACT

A new and distinct cultivar of *Hydrangea* plant named '200749077', characterized by its upright and mounded plant habit; strong stems; large durable leaves; large inflorescences; and inflorescences with blue-colored flowers.

1 Drawing Sheet

Botanical designation: *Hydrangea hybrida.*
Cultivar denomination: '200749077'.

BACKGROUND OF THE INVENTION

The present Invention relates to a new and distinct cultivar of *Hydrangea* plant, botanically known as *Hydrangea hybrida*, and hereinafter referred to by the cultivar name 200749077.

The new *Hydrangea* is a product of a planned breeding program conducted by the Inventor in Aalsmeer, The Netherlands and Glandorf, Germany. The objective of the breeding program was to create new stronger-growing *Hydrangeas* with attractive flower bract coloration and no vernalization requirement.

The new *Hydrangea* originated from a cross-pollination conducted in Aalsmeer, The Netherlands on Jul. 20, 1999 of a proprietary selection of *Hydrangea hybrida* identified as code number 97012-111, not patented, as the female, or seed, parent with a proprietary selection of *Hydrangea hybrida* identified as code number 98004, not patented, as the male, or pollen, parent. The cultivar 200749077 was discovered and selected by the Inventor as a single plant within the progeny of the stated cross-pollination in a controlled environment in Glandorf, Germany on Mar. 14, 2001.

Asexual reproduction of the new cultivar by vegetative cuttings at Glandorf, Germany, since Mar. 15, 2003, has shown that the unique features of this new *Hydrangea* are stable and reproduced true to type in successive generations.

SUMMARY OF THE INVENTION

Plants of the cultivar 200749077 have not been observed under all possible environmental conditions. The phenotype may vary somewhat with variations in environment such as temperature and light intensity without, however, any variance in genotype.

The following traits have been repeatedly observed and are determined to be the unique characteristics of '200749077'. These characteristics in combination distinguish '200749077 'as a new and distinct cultivar:

1. Upright and mounded plant habit.
2. Strong stems.

3. Large durable leaves.
4. Large inflorescences.
5. Inflorescences with blue-colored flowers.

Plants of the new *Hydrangea* differ from plants of female parent selection primarily in lateral branch thickness as plants of the new *Hydrangea* have thicker lateral branches than plants of the female parent selection. In addition, plants of the new *Hydrangea* have darker blue-colored flowers than plants of the female parent selection. Plants of the new *Hydrangea* differ from plants of male parent selection primarily in flower size as plants of the new *Hydrangea* have smaller flowers than plants of the male parent selection. In addition, plants of the new *Hydrangea* have darker blue-colored flowers than plants of the male parent selection.

Plants of the new *Hydrangea* can be compared to plants of the cultivar Adria, not patented. In side-by-side comparisons conducted in Glandorf, Germany, plants of the new *Hydrangea* differed from plants of the cultivar Adria in the following characteristics:

1. Plants of the new *Hydrangea* were larger and grew faster than plants of the cultivar Adria.
2. Plants of the new *Hydrangea* were more freely branching than plants of the cultivar Adria.
3. Plants of the new *Hydrangea* had stronger lateral branches than plants of the cultivar Adria.
4. Plants of the new *Hydrangea* had larger leaves with longer petioles than plants of the cultivar Adria.
5. Plants of the new *Hydrangea* were more freely flowering than plants of the cultivar Adria.

BRIEF DESCRIPTION OF THE PHOTOGRAPH

The accompanying colored photograph illustrates the unique appearance of the new cultivar, showing the colors as true as it is reasonably possible to obtain in colored reproductions of this type. Colors in the photograph may differ from the color values cited in the detailed botanical description which accurately describe the colors of the new *Hydrangea*. The photograph comprises a side perspective view of a typical plant of '200749077' grown in a container.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photograph and in the following description were grown in Glandorf, Germany, in 15-cm containers in a glass-covered greenhouse and under conditions which closely approximate commercial production conditions. During the production of the plants, day and night temperatures were about 17° C. Plants of the new *hydrangea* were grown in a soilless media with a pH level of about 4.4. Plants were about one year old when the photograph and description were taken. The photograph and description were taken during the late winter/early spring.

Botanical classification: *Hydrangea hybrida* cultivar 200749077.

Parentage:

*Male, or pollen, parent*.—Proprietary *Hydrangea hybrida* selection identified as code number 97012-111, not patented.

*Female, or seed, parent*.—Proprietary *Hydrangea hybrida* selection identified as code number 98004, not patented.

Propagation:

*Type cutting*.—By vegetative cuttings.

*Time to initiate roots, summer*.—About 14 days at 23° C.

*Time to initiate roots, winter*.—About 18 days at 18° C.

*Time to produce a rooted cutting or liner, summer*.—About four weeks at 23° C.

*Time to produce a rooted cutting or liner, winter*.—About five weeks at 18° C.

*Root description*.—Thick; white to brown in color.

*Rooting habit*.—Freely branching; dense.

Plant description:

*Form/growth habit*.—Upright and mounded plant habit. Strong lateral branches; vigorous growth habit.

*Plant height, soil level to top of plant plane*.—About 25 to 30 cm.

*Plant diameter or area of spread*.—About 35 cm.

*Branching habit*.—When pinched, freely branching with about ten lateral branches per plant.

*Lateral branches*.—Length: About 18 to 23 cm. Diameter: About 5 mm. Internode length: About 3.5 cm. Texture: Smooth, glabrous. Strength: Strong. Color: Close to 146A.

*Foliage description*.—Leaves large, simple, opposite and durable. Length: About 12.5 cm. Width: About 8.5 cm. Shape: Elliptic. Apex: Acute. Base: Obtuse. Margin: Dentate. Texture, upper and lower surfaces: Smooth to rugose; glabrous. Venation pattern: Pinnate. Color: Developing and fully expanded foliage, upper surface: Close to 147A. Developing and fully expanded foliage, lower surface: Close to 147B. Venation, upper and lower surfaces: Close to 146A. Petiole: Length: About 2.5 cm. Diameter: About 4 mm. Texture, upper and lower surfaces: Smooth, glabrous. Color, upper and lower surfaces: Close to 146A.

Flower description:

*Flower type and habit*.—Single flat flowers arranged on terminal panicles; panicles large and globular. Flowers face upright to outward. Flowers persistent. Flowers not fragrant.

*Natural flowering season*.—Intermittent flowering during the summer in Northern Europe.

*Flower longevity*.—Flowers last about three months on the plant.

*Quantity of flowers*.—Freely flowering; about 80 per panicle.

*Panicle diameter*.—About 15 cm.

*Panicle height*.—About 9 cm.

*Flower diameter*.—About 4 cm.

*Flower depth* (*height*).—About 1 cm.

*Flower buds*.—Length: About 5 mm. Diameter: About 3 mm. Shape: Ovoid. Color: 145C.

*Petals*.—Arrangement: Five in a single whorl. Length: About 4 mm. Width: About 2 mm. Shape: Ovate. Apex: Acute. Base: Attenuate. Margin: Entire. Texture, upper and lower surfaces: Smooth, glabrous. Color: When opening, upper and lower surfaces: 145C. Fully opened, upper and lower surfaces: 106B.

*Sepals*.—Quantity per flower: Four, fused into a calyx. Length: About 1.5 to 2 cm. Width: About 2 cm. Shape: Deltoid. Apex: Retuse. Base: Cuneate. Margin: Entire; undulate. Texture, upper and lower surfaces: Smooth, glabrous. Color: When opening, upper and lower surfaces: 145C. Fully opened, upper surface: 104B. Fully opened, lower surface: 106C.

*Pedicels*.—Angle: Erect to about 45° from vertical. Strength: Strong. Length: About 1.5 to 3 cm. Diameter: About 2 to 6 mm. Color: 107C.

*Reproductive organs*.—Stamens: Quantity per flower: About three. Anther shape: Conical. Anther length: About 1 mm. Anther color: 115A. Pollen amount: Abundant. Pollen color: Close to 155D. Pistils: Pistil quantity per flower: About eight. Pistil length: About 3 to 4 mm. Stigma shape: Oval. Stigma color: 150D. Style length: About 2 to 3 mm. Style color: 150D. Ovary color: 150D. Seed: Length: About 1 mm. Diameter: About 0.2 mm. Color: Brownish.

Disease/pest resistance: Under commercial production conditions, plants of the new *Hydrangea* have not been observed to be resistant to pathogens or pests common to *Hydrangea*.

Temperature tolerance: Plants of the new *Hydrangea* have been shown to be tolerant to temperatures ranging from about 3 to about 38° C.

It is claimed:

1. A new and distinct cultivar of *Hydrangea* plant named '200749077', as illustrated and described.

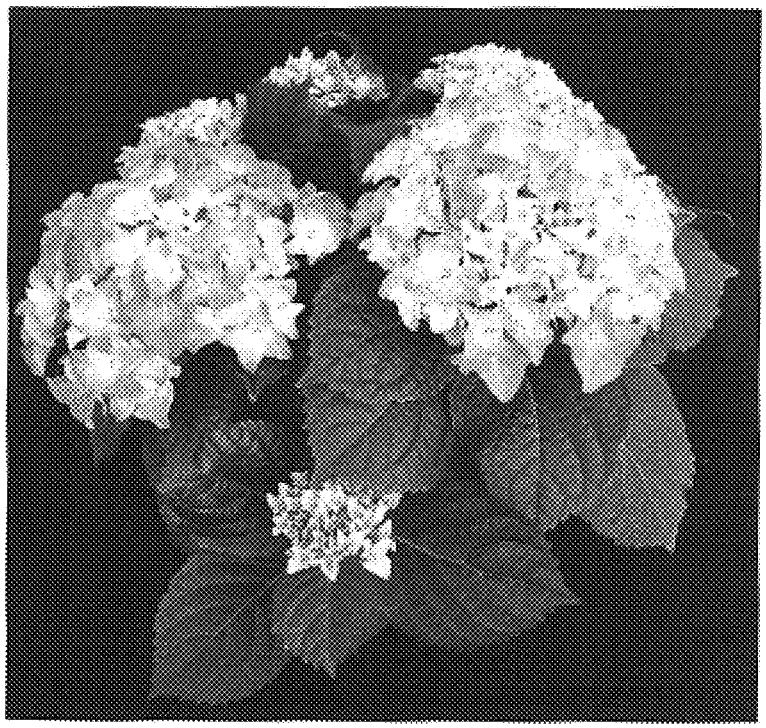

* * * * *